United States Patent [19]

Anderson et al.

[11] Patent Number: 5,464,825
[45] Date of Patent: Nov. 7, 1995

[54] RAISING GLUTATHIONE EQUIVALENT LEVELS USING N-ACYL GLUTATHIONE MONOESTERS

[75] Inventors: Mary Anderson; Alton Meister, both of New York; Ellen J. Levy, Brooklyn, all of N.Y.

[73] Assignee: Cornell Research Foundation, Inc., Ithaca, N.Y.

[21] Appl. No.: 226,409

[22] Filed: Apr. 12, 1994

Related U.S. Application Data

[63] Continuation of Ser. No. 102,962, Aug. 6, 1993, abandoned, which is a continuation of Ser. No. 988,025, Dec. 9, 1992, abandoned, which is a continuation of Ser. No. 673,811, Mar. 14, 1991, abandoned.

[51] Int. Cl.⁶ .......................... A61K 38/00; C07K 5/00; C07K 7/00; C07K 17/00
[52] U.S. Cl. ........................................ 514/18; 530/331
[58] Field of Search ........................ 530/331; 514/18

[56] References Cited

U.S. PATENT DOCUMENTS

| | | | |
|---|---|---|---|
| 2,209,299 | 7/1940 | Schoeller et al. | 514/18 |
| 2,760,956 | 8/1956 | Brick | 514/18 |
| 2,938,023 | 5/1960 | Weygand et al. | 514/18 |
| 3,882,097 | 5/1975 | Pfister, III et al. | 514/18 |
| 3,950,387 | 4/1976 | Joulie et al. | 514/18 |
| 3,984,569 | 10/1976 | Kalopissis et al. | 514/18 |
| 4,643,990 | 2/1987 | Umehara et al. | 514/18 |
| 4,709,013 | 11/1987 | Nagano | 530/331 |
| 4,710,480 | 12/1987 | Meister | 514/18 |
| 4,710,489 | 12/1987 | Meister | 514/18 |
| 4,784,685 | 11/1988 | Meister | 71/106 |
| 4,879,370 | 11/1989 | Meister | 530/331 |
| 4,927,808 | 5/1990 | Kitahara et al. | 514/18 |
| 4,968,671 | 11/1990 | Asano et al. | 514/18 |

OTHER PUBLICATIONS

Meister, Metabolism & Function of Glutathione, Chapter 11, *Coenzymes & Cofactors*, vol. III, (1989).
Kalebic et al., *Proc. Natl. Acad. Sci. USA*, 88:986–990 (1991).
1991 *FASEB Abstract*, 1 page.

*Primary Examiner*—Jill Warden
*Assistant Examiner*—Sheela J. Huff

[57] ABSTRACT

The preparation and use of N-acyl glutathione monoalkyl esters to provide increased intracellular levels of glutathione or glutathione equivalents, e.g. N-acyl glutathione or glutathione monoalkyl esters.

7 Claims, 2 Drawing Sheets

RAISING GLUTATHIONE EQUIVALENT LEVELS USING N-ACYL GLUTATHIONE MONOESTERS

This invention was made with Government support under Grant Nos. 2R37DK12034 and T32DK07152, awarded by the National Institutes of Health. The Government has certain rights in the invention. This application is a continuation, of application Ser. No. 08/102,962, filed Aug. 6, 1993, now abandoned, which is a continuation of Ser. No. 07/988,025, filed Dec. 9, 1992, now abandoned which is a continuation of application Ser. No. 07/673,811, filed Mar. 14, 1991, now abandoned.

BACKGROUND OF THE INVENTION

It is well known that glutathione is a tripeptide thiol (L-γ-glutamyl-L-cysteinylglycine; GSH) which is found in virtually all cells and functions in metabolism, transport, and cellular protection. GSH is a coenzyme for several enzymatic reactions; GSH is involved in the reduction of the disulfide linkages of proteins and other molecules, in the synthesis of deoxyribonucleotide precursors of DNA, in the protection of cells against the effects of free radicals and of reactive oxygen intermediates like peroxides, and in the transport of amino acids.

Modifications of glutathione metabolism can be achieved by the administration of selective enzyme inhibitors to decrease intracellular GSH levels, or by administration of compounds that increase GSH synthesis. Such effects are useful in chemotherapy and radiation therapy and in protecting cells against the toxic effects of drugs, other foreign compounds and oxygen, and in preventing the expression of latent HIV in AIDS. The many functions of GSH are important in many fields of biology enzymology and transport, pharmacology, radiation biology, cancer therapy, toxicology, endocrinology, microbiology, agriculture, virology, and immunology. The enzymology, metabolism and functions of GSH are outlined in Meister. "Metabolism and Function of Glutathione", in "Glutathione: Chemical, Biochemical, and Medical Aspects" Part A. pages 367–474, volume III of Coenzymes and Cofactors, eds. D. Dolphin, R. Poulseon, O. Avramovic; John Wiley, New York, 1989.

Modification of GSH metabolism to deplete or increase cellular GSH may serve various purposes. For example, it is well known that thiols protect cells against the effects of irradiation. Since decreasing cellular GSH levels makes cells more susceptible to irradiation, GSH depletion is useful in chemotherapeutic situations in which the cells to be destroyed and the cells to be spared have substantially different quantitative requirements for GSH. Depletion of GSH by inhibition of its synthesis also serves as a valuable adjuvant in chemotherapy with drugs that are detoxified by reactions involving GSH.

Development of resistance to a drug or to radiation therapy may be associated with an increase in cellular GSH. GSH is involved in the detoxification of many drugs, and it is known that a significant pathway of acetaminophen detoxification involved conjugation with GSH.

GSH is required for lymphocyte proliferation. Depletion of lymphocyte GSH by treatment with a selective inhibitor of GSH synthesis, L-buthionine-SR-sulfoximine (BSO), inhibits proliferation. Conversely, supplying GSH permits lymphocyte proliferation.

When lymphocytic cells containing HIV (a latent model of HIV infection ) are treated with thiols, such as N-acetyl cysteine, GSH and GSH monoethyl ester, and stimulated, they produce little virus in comparison with the cells that are not thiol treated.

Treatment with a thiazolidine such as L-2-oxothiazolidine-4-carboxylic acid, may be of value to patients with liver disease and to premature infants who may be deficient in the utilization of methionine sulfur for cysteine formation, and thus in GSH synthesis. The effectiveness of such a thiazolidine as an intracellular cysteine precursor depends on the presence of 5-oxoprolinase, an enzyme activity found in almost all animal cells. This enzyme also occurs in plants, suggesting that such a thiazolidine, and hence glutathione, may be useful as a safener in agriculture to protect crop plants against the toxic effects of herbicides.

Various methods are known to increase cellular levels of glutathione. GSH is composed of three amino acids: glutamic acid, cysteine, and glycine. Administration to animals of the amino acid precursors of GSH may produce an increase in cellular GSH; however, there is a limit to the effectiveness of this procedure. Concentration of cellular GSH are dependent on the supply of cysteine, which is derived from dietary protein and by trans-sulfuration from methionine in the liver. Administration of cysteine is not a good method for increasing GSH levels because cysteine is rapidly metabolized and it is also toxic. Administration to animals of compounds that are transported into cells and converted intracellularly into cysteine is sometimes useful in increasing cellular GSH. For example, the thiazolidine, L-2-oxothiazolidine-4-carboxylic acid, is transported into the cell, where it is converted by 5-oxoprolinase into L-cystine, which is rapidly used for GSH synthesis.

Another way in which tissue GSH concentration may be increased is by administration of γ-glutamyl amino acid is transported intact and serves as a substrate of GSH synthetase. This method is effective for cells which have a γ-glutamyl amino acid transport system. It is also known that administration of N-acetyl-L-cysteine increases tissue concentrations of GSH. This latter method requires a deacetylase and may be limited by toxicity of N-acetyl-L-cysteines.

That the administration of GSH itself might lead to increase GSH levels has also been considered. However, there is little published data that shows intact GSH enters cells. There are several reports on particular biological systems indicating that GSH itself is not transported into cells. A very little GSH may be transported into some cells, such as intestinal cells. However, the increase in cellular GSH sometimes found in some cells after the administration of GSH is due to (a) extracellular breakdown of GSH, (b) transport of free amino acids or dipeptides derived for GSH extracellularly, and (c) intracellular resynthesis of GSH.

These previous methods of increasing intracellular GSH levels are disadvantageous in the areas of efficiency, toxicity, limits on effective concentration obtainable, etc. as discussed heretofore. In addition, the known methods which depend on synthesis of GSH by increasing the supply of substrates to the synthetases involved, depend on the presence of the synthetases, one of which is subject to feedback inhibition by GSH.

The administration of GSH monoesters increases cellular GSH in many cells, without the need from the enzymes of GSH synthesis. It is effective in preventing acetaminophen and some heavy metal poisoning.

Accordingly, an object of the invention is to provide a method for increasing the intracellular levels of GSH by delivering intact GSH to cells, rather than its amino acid or dipeptide substrates.

A further object of the invention is to provide pure derivatives of GSH, the use thereof in GSH delivery and a method for obtaining such pure derivatives.

Another object of the invention is to provide a method of increasing intracellular levels of GSH which is highly efficient and which does not depend on the presence of synthetases.

A further object of the present invention is to provide a method for increasing the intracellular levels of GSH with toxic effects of other methods.

Still another object of the invention is to provide a method for efficiency and rapidly increasing cellular GSH levels for any purpose for which elevated GSH levels are desired in the prior art, such as for drug detoxification, cellular protection against oxygen and its metabolites such as peroxides, free radicals, or foreign compounds, etc, and in lymphocyte function, in the treatment of AIDS and other viral infections, etc.

SUMMARY OF THE INVENTION

This invention relates to a method for increasing intracellular GSH levels or intracellular levels of glutathione equivalents i.e. N-acyl glutathiones or glutathione monoalkyl esters by administering an alkyl monoester of N-acyl glutathione, with the esterification occurring at the glycine carboxylic acid group. Such acylated esters are transported into cells, for example, liver and kidney cells and are de-esterified and de-acetylated within the cells, leading to increased cellular levels of GSH. NAG and GSH monoester are also formed in the cells, providing a further source of GSH. The alkyl group can contain 1 to 10 carbon atoms, preferably 1 to 4 carbon atoms. The acyl group, while preferably acetyl, can contain 1 to 9 carbon atoms, preferably 1 to 4 carbon atoms, and can be in a straight or branched chain acyl group, for example, formyl, acetyl, propyl isopropyl.

By the present method involving administration of N-acyl GSH esters, increased levels of GSH are provided in an efficient, rapid manner.

In addition, the present invention provides the pure N-acyl GSH esters, and a method to produce them as disclosed hereinafter.

It is noted that the glutathione monoalkyl esters are described and claimed, for example, in U.S. Pat. Nos. 4,710,489; 4,784,685 and 4,879,370, which are hereby incorporated by reference. The N-acyl glutathione esters of the present invention have the same utilities described therein for the monoesters.

DESCRIPTION OF PREFERRED EMBODIMENTS

Figure 1:
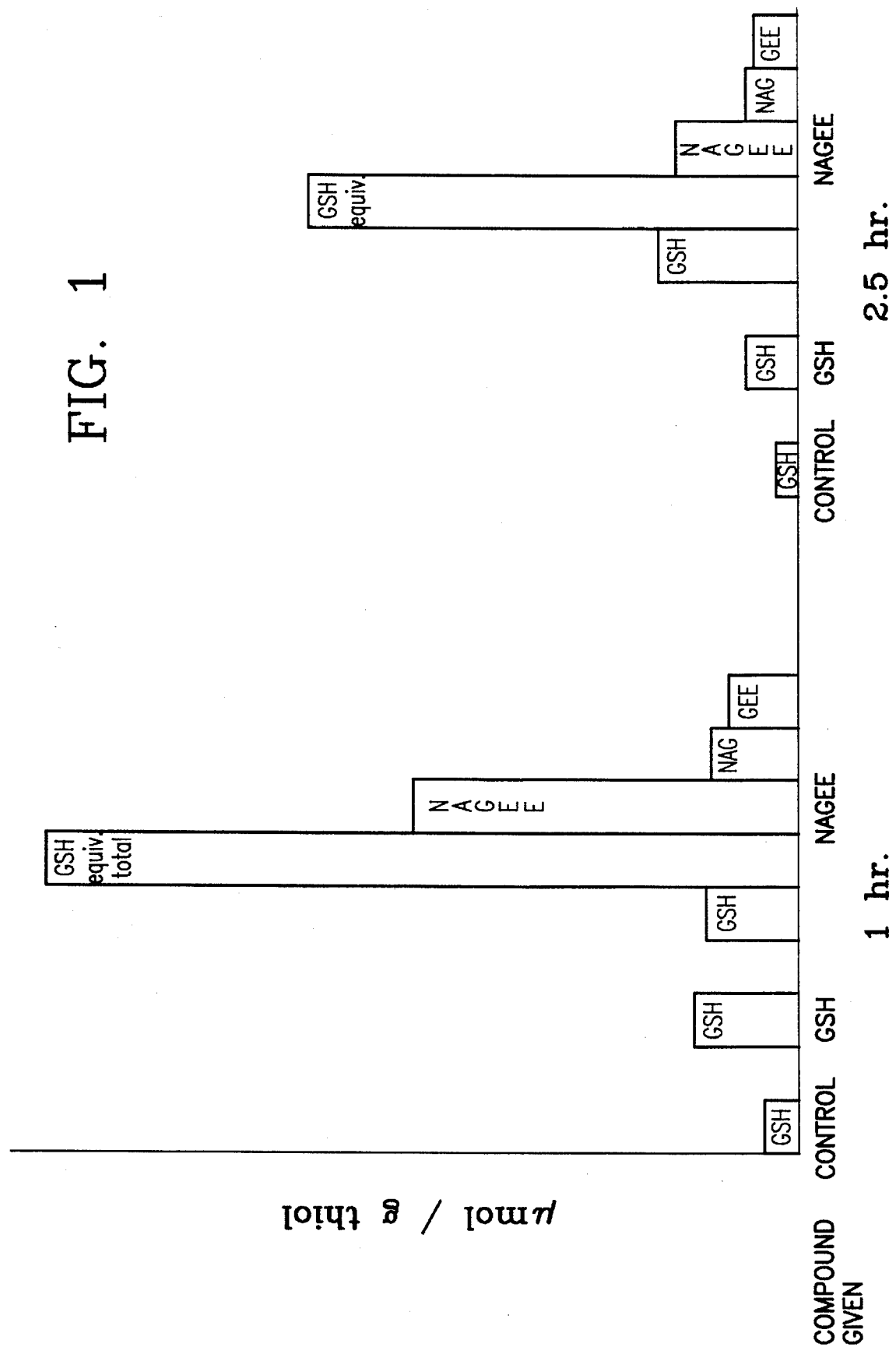
FIG. 1 is a graph plotting the GSH, N-acetyl GSH, N-acetyl GSH monoester and GSH monoester levels of the kidney of fasted, BSO treated, mice given N-acetyl GSH monoester and GSH itself in comparison with controls.

By the present method, esterified N-acyl GSH acyl monoester is transported intact into the cell, where it is de-esterified and de-acylated by the actions of enzymes; thus leading to increased cellular levels of GSH, as well as N-acetyl GSH and GSH monoester.

GSH has one amino group. GSH has two carboxyl groups, one on the glutamic acid residue and one on the glycine residue. The compounds used in the present method are alkyl esters of N-acetyl GSH in which only the glycine carboxyl group is esterified. Thus, the compounds used in the present invention have the structure:

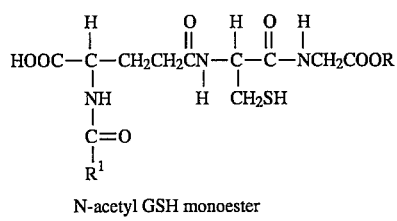

N-acetyl GSH monoester

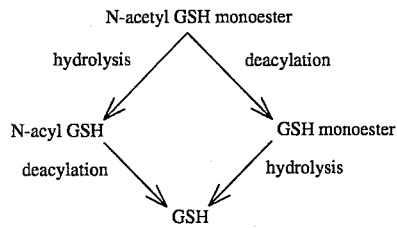

wherein R is an alkyl group containing 1 to 10 carbon atoms, and $R^1$ is hydrogen or an alkyl group containing 1 to 9 carbon atoms. Pharmaceutically acceptable salts of the above compounds are within the scope of the present invention.

The alkyl group of the N-acetyl GSH monoalkyl ester according to the invention is a saturated, straight or branched, alkyl group of 1 to 10 carbon atoms preferably 1 to 4 carbon atoms and preferably a saturated straight alkyl group such as methyl, ethyl, propyl, butyl, pentyl, hexyl, heptyl, octyl, nonyl, or decyl and a saturated branched alkyl group such as isopropyl, isobutyl, sec-butyl, tert-butyl or isopentyl. Among them, methyl, ethyl, isopropyl, propyl and isobutyl are especially suitable for medical use, because their intracellular GSH level elevating activity is excellent and they are easily obtainable in the crystalline form.

Similarly, the hydrocarbon portion of the acyl group $R^1$ above, (when not hydrogen) is a saturated, straight or branch, alkyl group of 1 to 9 carbon atoms, preferably 1 to 3 carbon atoms, and can likewise be methyl, ethyl, propyl, butyl, pentyl, hexyl, etc. or isopropyl, isobutyl sec-butyl, etc.

The source of GSH or GSH monoester used in the present invention is not important, and thus GSH or GSH monoester may be synthesized or isolated by conventional methods in the art or purchased.

The esterification procedure used can be selected from those conventional in the art. Preferably, the esters are subjected to sufficient purification so that on a weight basis, the monoester is at least 98% pure, preferably at east 90% pure. An overall process to yield pure free base monoester is set forth in synthesis examples hereinafter. The free monoester is acylated and purified as set in the examples hereinafter.

The N-acyl GSH monoester can be chemically prepared from the free GSH monoester by reacting GSH monoester with the appropriate known acylating agent in a manner known in the art, for example for an acetyl group, with acetic anhydride in formic acid. GSH monoester is prepared by reacting GSH with an alcohol (ROH in which R is an alkyl group of 1 to 10 carbon atoms) containing hydrogen chloride or sulfuric acid at temperatures from 0° to 35° C. over a period of time from a few hours to several days to give the hydrochloride or hemisulfate of the GSH mono-ethyl ester. GSH monoester hydrochloride or preferably hemisulfate is converted into the free monoalkyl ester by conventional methods in the art as described in synthesis hereinafter. The free GSH monoester is then reacted at temperatures from 4° to 35° C. over a period of time from minutes to hours, an example is set forth in Synthesis hereinafter. The N-acyl GSH monoester is further purified using a method for metal complexing, such as binding of contaminating metal to Chelex resin. This purification step is necessary to remove metals, especially iron from the preparation which may produce toxicity.

As the alcohol, there may be used the one corresponding to the objective N-acyl ester, and preferred are a straight saturated alcohol such a methyl alcohol, ethyl alcohol, propyl alcohol, butyl alcohol, pentyl alcohol, hexyl alcohol, heptyl alcohol, octyl alcohol, nonyl alcohol or decyl alcohol and a branched saturated alcohol such as isopropyl alcohol, isobutyl alcohol, sec-butyl alcohol, tert-butyl alcohol, isopentyl alcohol or neopentyl alcohol.

The N-acyl monoalkyl esters of GSH are typically administered by injection after dissolution in water. However, the N-acyl ester should also be effective after oral administration. The N-acyl esters can be admixed with suitable pharmaceutically acceptable carriers such as the aforementioned water or physiological saline solution or sodium bicarbonate solutions in the preparation of liquid formulations or with lactose, sucrose, starch, talc or the like in formulating powders.

A suitable therapeutically effective dosage can be selected based on routine experimentation, particularly in view of prior art uses for GSH and GSH monoester and the examples hereinafter, bearing in mind the approximately stoichiometric intracellular, hydrolysis and acylation believed to occur. In any event, one can monitor GSH or N-acyl GSH or GSH monoester level in the patient or use other parameters of effectiveness depending on the nature of the treatment. At this time, a suggested dosage is about 0.5 to 10 millimoles of N-acyl monoester per kg of body weight, preferably about 1 to 5 millimoles of N-acyl monoester per kg of body weight, one to six times a day.

Administration is carried out to typically result in increased intracellular levels of GSH, N-acetyl GSH, GSH monoester, and N-acetyl GSH monoester within 0.5 to 2.5 hours after administration.

Although the precise mechanism of he reactions are not known, the increase in intracellular GSH, and appearance of N-acyl GSH and GSH monoester, is interpreted to indicate that the administered N-acyl GSH monoester is transported into the cells of at least the liver and kidney where it is hydrolyzed to GSH, N-acyl GSH, and/or GSH monoester. Such hydrolysis has been demonstrated in in vitro experiments in which N-acetyl GSH mono esters were incubated with homogenates of kidney and livers.

Having described in broader terms embodiments of the present invention, the following more detailed description is provided with reference to specific examples.

SYNTHESIS, EXAMPLE 1

Preparation of N-Acetyl Glutathione Monoethyl Ester (NAGEE)

1. Preparation of free GSH monoethyl ester (L-γ-glutamyl-L-cysteinyl glycyl ethyl ester). Glutathione monoethyl ester (GEE) hemihydrosulfate is converted to the free base. GEE (5 g; 13 mmol) is dissolved in 150 ml cold distilled water and Dowex 1-$HCO_3$ (7 g per 2.6 mmol GEE) is added. The mixture is stirred for a few minutes, until the bubbling stops. An aliquot of the supernatant (obtained by centrifugation) is assayed for sulfate (using barium chloride). If there is no sulfate in solution (i.e.. the sulfate is bound to the Dowex 1), the mixture is filtered under reduced pressure; the receiving vessel contains Chelex $H^+$ (about 2 g per 2.5 mmol of GEE sulfate). The Dowex 1 is rapidly rinsed with distilled water and the eluates are combined. The Chelex is then removed by filtration under reduced pressure with several water rinses. The eluate is dried by lyophilization.

2. GEE free base (3.5 g; 10.4 mmol) is dissolved in 96–100% formic acid (32 ml; about 850 mmol) in a liter Erlenmeyer flask. The reaction is cooled to approximately 4° C. Acetic anhydride (16–18 ml; 170–191 mmol) is added to the ester solution and mixed. The reaction is agitated at 27° to 30° C. After about 0.5 hour, the reaction is complete as determined by a lack of reaction with ninhydrin. Anhydrous diethyl ether is added to give a final volume of 800 ml and a colorless gel forms. The gel is filtered under reduced pressure and washed extensively with diethyl ether until a white powdery product is obtained. This solid is dried with nitrogen gas followed by more diethyl ether washes. The white solid is then dried with a stream of nitrogen gas and powdered. The N-acetyl glutathione monoethyl ester (NAGEE) product (yield about 60%; 2.2 g; 5.8 mmol) is then dried and stored under reduced pressure over $P_2O_5$.

3. The NAGEE is further purified by dissolving 1 g (2.64 mmol) in 8 ml of distilled, deionized water. This solution is applied to a Chelex $Na^+$ column (1.5×22 cm; pH 5.5). The NAGEE elutes rapidly with water. The NAGEE fractions are combined and dried by lyophilization (yield about 80%).

Note: All glassware for steps 2 and 3 are cleaned by boiling in 0.5 M sodium EDTA and then washing with distilled, deionized water. The glassware for step 2 is additionally rinsed with small portions of ethanol, and then formic acid.

EXAMPLE 1

Figure 2:
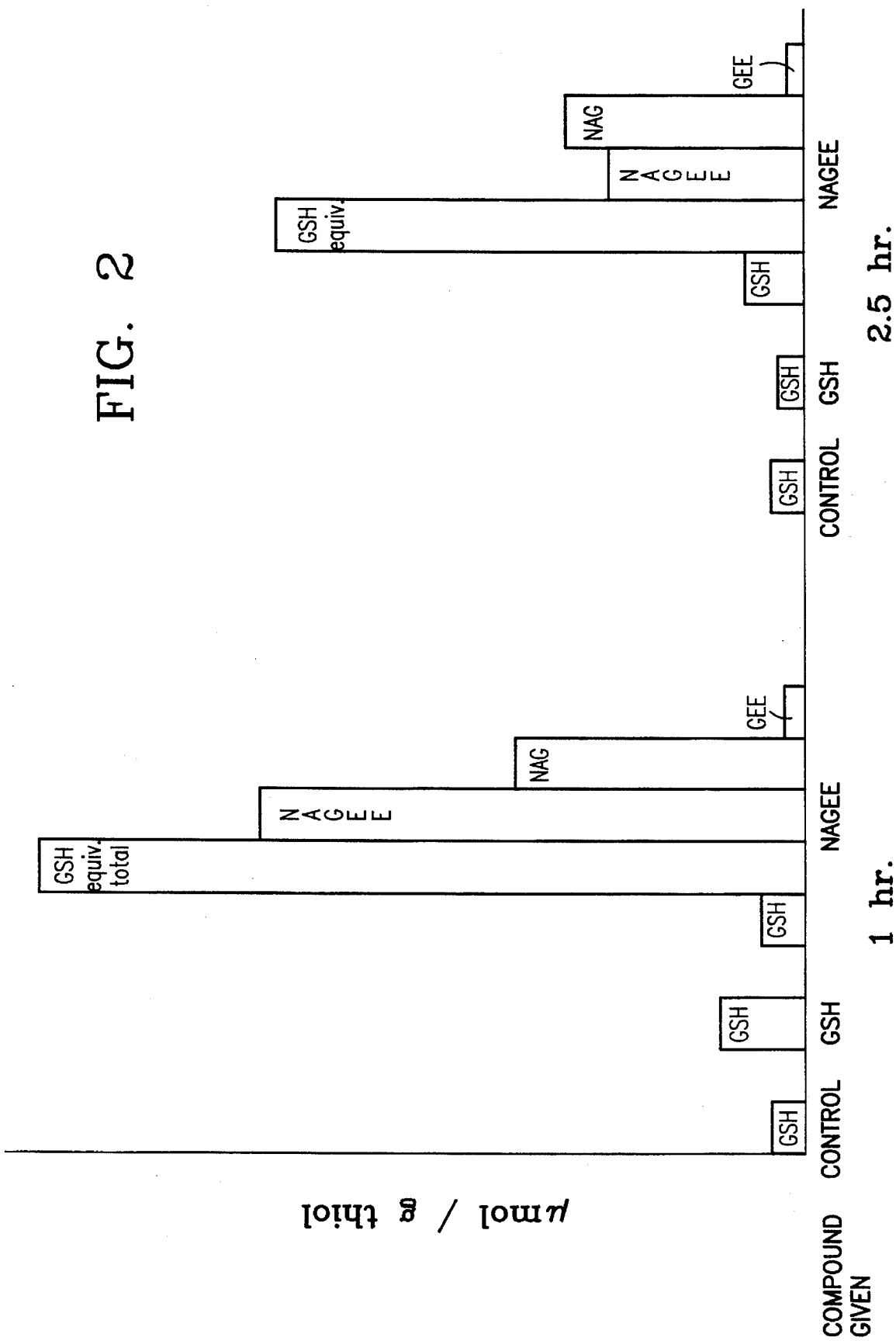
FIG. 2 is a graph plotting the GSH, N-acetyl GSH, N-acetyl GSH monoester and GSH monoester levels of the liver of fasted, BSO treated, mice given N-acetyl GSH monoester and GSH itself in comparison with controls.

The N-acetyl GSH monoethyl ester was used. A solution of N-acetyl GSH monoester was prepared in aseptic water. Mice weighing 18 to 25 grams, obtained from Taconic Farms, Inc., (TAC:(SWFBR)), were fasted for 18 hours before injection with NAGEE. At the time of fasting, the drinking water contains 10 mM L-buthionine-SR-sulfoximine (BSO). All mice are injected with L-buthionine-SR-sulfoximine (BSO) (2 millimoles per kilogram; intraperitoneally) 13 hours before NAGEE injection. The mice are injected again with L-buthionine-SR-sulfoxminie (BSO) (2 millimoles per kg; subcutaneously) 3 hours prior to NAGEE injection. NAGEE or GSH are administered intraperitoneally (10 mmol/kg; the pH of the solution is adjusted to about 7 with sodium hydroxide). The GSH solution also contains ethanol at 10 mmol/kg. Control mice are given equivalent volumes of 0.9% sodium chloride. The mice were then injected intraperitoneally with the N-acetyl GSH monoethyl ester in a dose of 10 millimoles per kilogram. At intervals, as shown in FIGS. 1 and 2, the mice were decapitated and the kidney and liver tissues were removed and analyzed for NAGEE, GSH, N-acetyl GSH and GSH monoethyl ester. Using groups of 4 or 5 mice each, values are given as means plus or minus S.D.

As shown in FIGS. 1 and 2, the GSH level of the kidney treated with N-acetyl GSH monoethyl ester increased substantially 2.5 hours after administration. The levels then declined at 5 hours. Also, substantial levels of GSH monoethyl ester, NAGEE and NAG, not naturally occuring compounds were found. The liver levels of GSH increased moderately at 2.5 hours, while those of N-acetyl GSH increased dramatically at 1 and 2.5 hours; a little GSH mono-ethyl ester was found in the liver. Controls and BSO controls received 0.15 M sodium chloride.

COMPARATIVE EXAMPLE 1

Example 1 was repeated with the substitution of GSH for N-acetyl GSH monoethyl ester. As shown in FIGS. 1 and 2, no effect was seen in the glutathione levels of the liver of the controls and only a slight effect is noted with GSH itself in the kidney, as compared to the controls in which there is essentially no change.

| | μmol/g (thiol) |
|---|---|
| | Kidney |
| COMPOUND GIVEN | 1 hour |
| CONTROL | 0.17 (GSH) |
| GSH | 1.9 (GSH) |
| NAGEE | 1.6 (GSH) |
| | 10.51 (GSH equivalents total) |
| | 5.54 (NAGEE) |
| | 1.43 (NAG) |
| | 0.92 (GEE) |
| | 2.5 hours |
| CONTROL | 0.14 |
| GSH | 1.01 |
| NAGEE | 2.3 (GSH) |
| | 5.67 (GSH equivalents total) |
| | 2.10 (NAGEE) |
| | 0.79 (NAG) |
| | 0.52 (GEE) |
| | Liver |
| | 1 hour |
| CONTROL | 0.46 (GSH) |
| GSH | 1.38 (GSH) |
| NAGEE | 0.45 (GSH) |
| | 14.28 (GSH equivalents total) |
| | 8.85 (NAGEE) |
| | 4.80 (NAG) |
| | 0.18 (GEE) |
| | 2.5 hours |
| CONTROL | 0.65 (GSH) |
| GSH | 0.45 (GSH) |
| NAGEE | 0.71 (GSH) |
| | 7.17 (GSH equivalent total) |
| | 2.93 (NAGEE) |
| | 3.38 (NAG) |
| | 0.15 (GEE) |

The findings disclosed herein indicate that the administered N-acetyl GSH monoester is transported into the cells of the liver and kidney where it is hydrolyzed to GSH; N-acetyl GSH and GSH monoester are also formed. The studies in which mice were pretreated with L-buthionine-SR-sulfoximine provide strong evidence for the transport of N-acetyl GSH monoesters; under these conditions, the synthesis of GSH from its constituent amino acids is markedly inhibited. Also the finding of N-acetyl GSH and GSH monoester in tissues is strong evidence that N-acetyl GSH monoester is transported into cells and hydrolyzed. It is also seen that intact GSH is not delivered into the cell, since GSH synthesis is markedly inhibited by L-buthionine-SR-sulfoximine. Thus, the present method permits increasing the intracellular GSH level in instances where a deficiency of the necessary synthetase for GSH exists, or where a higher level of GSH or N-acetyl GSH is beneficial.

It is to be understood that the invention is not limited to the particular details described, for obvious modifications will occur to a person skilled in the art. In addition, the N-acyl monoesters of the present invention could be employed as safeners for plant crops by being administered thereto or to seeds prior to planting through absorbable liquid applications to protect the plants against the effects of herbicides being applied to combat weeds which are or might grow among the plant crops.

Variations of the invention will be apparent to the skilled artisan.

What is claimed is:

1. Substantially pure N-acyl monoalkyl glutathione monoester, only the glycine carboxyl group being esterified, where the acyl group contains 1 to 10 carbon atoms and the monoalkyl group contains 1 to 9 carbon atoms.

2. The compound of claim 1 where the acyl group is acetyl and the monoalkyl group contains 1 to 4 carbon atoms.

3. The compound of claim 2 where the monoalkyl group is ethyl or isopropyl.

4. A method for increasing cellular levels of glutathione or a glutathione equivalent in animals comprising:

administering a compound as in claim 1 in an amount effective to increase intracellular levels of glutathione or a glutathione equivalent whereby said monoester is transported into cells of said animals and hydrolyzed intracellularly to glutathione or a glutathione equivalent.

5. The method of claim 4 wherein said compound is administered in a dosage of 0.5 to 10 millimoles per kilogram of animal body weight.

6. The method of claim 4 where the compound is orally administered to said animal to enhance cellular glutathione or glutathione equivalent levels.

7. The method of claim 4 where the compound is injected into said animal to enhance cellular glutathione or glutathione equivalent levels.

* * * * *